(12) United States Patent
Cho et al.

(10) Patent No.: US 10,321,688 B2
(45) Date of Patent: Jun. 18, 2019

(54) METHOD FOR PREPARING STERILIZING DEODORANT AND STERILIZING DEODORANT PREPARED THEREBY

(71) Applicants: Je Shu Cho, Seoul (KR); Yong Hwan Ko, Anyang-si (KR)

(72) Inventors: Je Shu Cho, Seoul (KR); Yong Hwan Ko, Anyang-si (KR)

(*) Notice: Subject to any disclaimer, the term of this patent is extended or adjusted under 35 U.S.C. 154(b) by 22 days.

(21) Appl. No.: 15/663,851

(22) Filed: Jul. 31, 2017

(65) Prior Publication Data
US 2018/0027821 A1 Feb. 1, 2018

(30) Foreign Application Priority Data

Aug. 1, 2016 (KR) .................. 10-2016-0098123

(51) Int. Cl.
| | |
|---|---|
| *A61L 9/01* | (2006.01) |
| *A61L 9/013* | (2006.01) |
| *A01N 59/00* | (2006.01) |
| *A01N 59/16* | (2006.01) |
| *A01N 63/00* | (2006.01) |
| *A01N 65/06* | (2009.01) |
| *A01N 65/08* | (2009.01) |
| *A01N 65/20* | (2009.01) |
| *B01D 17/06* | (2006.01) |

(52) U.S. Cl.
CPC ............. *A01N 65/20* (2013.01); *A01N 59/00* (2013.01); *A01N 59/16* (2013.01); *A01N 63/00* (2013.01); *A01N 65/06* (2013.01); *A01N 65/08* (2013.01); *A61L 9/01* (2013.01); *A61L 9/013* (2013.01); *B01D 17/06* (2013.01)

(58) Field of Classification Search
CPC ........ A01N 65/06; A01N 65/08; A01N 65/20; A01N 59/16; A61L 9/00; A61L 9/01; A61L 9/013
See application file for complete search history.

(56) References Cited

FOREIGN PATENT DOCUMENTS

| KR | 20000074767 A | 12/2000 | |
|---|---|---|---|
| KR | 2012-0110429 | * 10/2012 | ............. A61L 9/013 |

OTHER PUBLICATIONS

Machine translation of KR 2012-0110429 to Ko et al., published Oct. 2012, as translated by InnovationQ, pp. 1-14.*

* cited by examiner

*Primary Examiner* — Kortney L. Klinkel
(74) *Attorney, Agent, or Firm* — Schmeiser, Olsen & Watts, LLP

(57) ABSTRACT

Provided is a method for preparing a sterilizing deodorant and a sterilizing deodorant prepared thereby. Particularly, the method for preparing a sterilizing deodorant includes preparing a first mixed solution containing a green tea leaf extract, a *Lespedeza bicolor* leaf extract, a *Chamaecyparis obtusa* leaf extract and a calcined shellfish shell powder, preparing a second mixed solution by adding germanium oxide and nano silver to the first mixed solution, and filtering the second mixed solution through a tourmaline filter. The germanium oxide and the nano silver are contained in a weight ratio of 1:0.5 to 1:3.

6 Claims, 1 Drawing Sheet

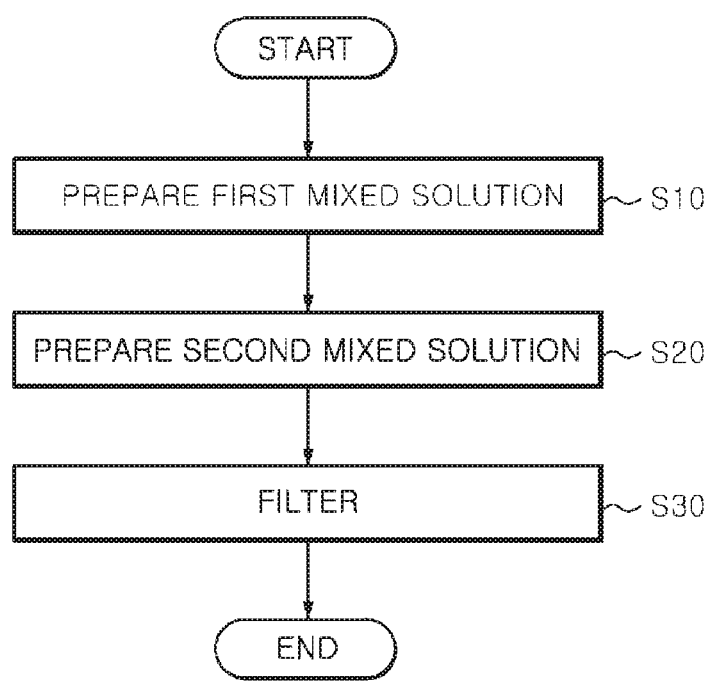

METHOD FOR PREPARING STERILIZING DEODORANT AND STERILIZING DEODORANT PREPARED THEREBY

CROSS-REFERENCE TO RELATED APPLICATION

This application claims priority to and the benefit of Korean Patent Application No. 10-2016-0098123, filed on Aug. 1, 2016, the disclosure of which is incorporated herein by reference in its entirety.

FIELD OF TECHNOLOGY

The following relates to a method for preparing a sterilizing deodorant and a sterilizing deodorant prepared thereby.

BACKGROUND

Since the 20$^{th}$ century, the dramatic development of scientific technology has led to mass-production of goods needed by people, and thus makes human life more convenient and enriched, and extends a human lifetime. Therefore, mass-consumption of a great deal of goods needed by humans has also begun.

The natural environment has gradually started to become polluted due to the mass production and mass consumption of goods needed by humans, and from the end of the 20$^{th}$ century to the present, the movement to protect nature and the environment is growing. However, such a movement is still insignificant.

The pollution of the natural environment generally occurred due to chemicals used in mass production of goods. In recent years, however, much pollution has also occurred due to disposal of abandoned goods after mass consumption. For such pollution of the natural environment, while only air, water, and soil pollution according to the subjects of pollution has been mentioned, in recent years, noise, foul smells and fumes, which adversely affect humans, have also been recognized as parts of pollution in addition to the air, water and soil pollution.

Among the types of pollution, the foul smells can be defined as all kinds of smells that are harmful to the human body or adversely affect the human body, as well as a simply unpleasant smell sensed by a nose, which is one of the human sensory organs.

To reduce such foul smells, a ventilation and dilution method of controlled-diffusing a smell by a hood, a duct and/or a high chimney, an absorbing method of passing a foul smelling substance through a cleaner for absorption and removal by a cleaning fluid, a freezing method of condensing and removing a foul smelling substance using a cooler, a combustion method of combusting a foul smelling substance by heating to a high temperature, a catalytic oxidation method of oxidizing foul smelling substances using a catalyst, or a chemical oxidation method of chemically oxidizing a foul smelling substance using ozone ($O_3$) and/or a chloride compound. In addition, a masking method of spraying an ingredient with a strong smell to cover a foul smell using fragrances such as vanillin, turpentine and benzyl acetate and a neutralizing method of mixing substances with different smells to remove or reduce a foul smell.

*Lespedeza bicolor* is a deciduous, broad-leaved plant in the legume family. *Lespedeza bicolor* is effective in alleviating fever and diuresis, good for the lungs, and has been used as a drug for treating coughs, pertussis and gonorrhea.

*Camellia sinensis* is an evergreen broad-leaved shrub, which grows to a height of approximately 60 to 90 cm. Its leaves are generally placed asymmetrically, and have a sharp-end oblong shape. There are green veins on its surface, a grey-green vein protruding on its back side, and no hair on both sides. Flowers bloom in October to November, are 3 to 5 cm in diameter, white and fragrant, have 1 to 3 axillaries, hanging at the end of the branch. The fruit is ripe in the autumn of the following year and the seed is round and hard. *Camellia sinensis* leaves (or green tea leaves) contain caffeine, tannins, nitrogen, proteins, vitamins and inorganic salts, and are known to have beneficial pharmacological actions on the human body, such as arousal, diuresis, heart stimulation, detoxification and fatigue recovery, etc.

*Chamaecyparis obtusa* is also called Hinoki cypress having a 30 to 40 m height and a 1 to 2 m width. The bark is reddish brown, and small needle-like leaves densely populate the branches. Small flowers bloom on branches in the spring, and green cones ripen to red in October. The cones are 1 cm in diameter and consist of 7 to 9 shield-like scales. Leaves and wood contain 1% essential oils and are used for medicinal purposes.

Shellfish is the generic name for the mollusks with shells in the phylum Mollusca. Shellfish largely includes bivalves, gastropods and scaphopods. A shell of the shellfish is strongly alkaline, and contains far-infrared radiation substances such as calcium oxide (CaO) and magnesium oxide (MgO).

In embodiments of the present invention, the shell of the shellfish rich in far-infrared radiation substances may be calcinated to further improve an effect on far-infrared radiation. That is, in the present invention, shell powder of the shellfish calcinated to improve an effect of far-infrared radiation may be obtained by calcinating any one selected from a clam shell, an oyster shell, and a conch shell for 30 minutes to 1 hour at 800 to 900° C., cooling the calcined product to 20 to 25° C., and grinding it into 100 to 200-mesh powder.

The background art related to embodiments of the present invention has been disclosed in Korean Unexamined Patent Application Publication No. 2000-0074767 (published on Dec. 15, 2000, Patent Title: Strong Deodorant Maksumsuk Heredity).

SUMMARY

An aspect relates to a method for preparing a sterilizing deodorant having an excellent sterilizing effect and foul smell removing efficiency.

The following is also directed to providing a method for preparing a sterilizing deodorant having excellent far-infrared radiation and anionic radiation effects.

The following is also directed to providing a method for preparing a sterilizing deodorant having excellent miscibility, productivity and economic feasibility.

The following is also directed to providing a method for preparing a sterilizing deodorant which is harmless to humans, and is very environmentally friendly.

The following is also directed to providing a method for preparing a sterilizing deodorant capable of removing a foul smell from various substances and exhibiting a sterilizing effect.

The following is also directed to providing a method for preparing a sterilizing deodorant having excellent sustainability of sterilizing and foul smell removing effects.

The following is also directed to providing a sterilizing deodorant prepared by the method of preparing a sterilizing deodorant.

One aspect of the following provides a method for preparing a sterilizing deodorant. In one exemplary embodiment, the method for preparing a sterilizing deodorant includes preparing a first mixed solution containing a green tea leaf extract, a *Lespedeza bicolor* leaf extract, a *Chamaecyparis obtusa* leaf extract and a calcined shellfish shell powder; preparing a second mixed solution by adding germanium oxide and nano silver to the first mixed solution; and filtering the second mixed solution through a tourmaline filter, and the germanium oxide and the nano silver are contained at a weight ratio of 1:0.5 to 1:3.

In one exemplary embodiment, the first mixed solution is prepared by preparing a first mixture by mixing 100 parts by weight of a green tea leaf extract, 10 to 50 parts by weight of a *Lespedeza bicolor* leaf extract, 10 to 50 parts by weight of a *Chamaecyparis obtusa* leaf extract and 10 to 70 parts by weight of a calcined shellfish shell powder; and treating the first mixture with any one of electrical energy and magnetic energy. The treatment with electrical energy is treating the first mixture for 1 to 6 hours in an electric field of 100 to 1000 kV, and the treatment with magnetic energy is treating the first mixture for 12 to 24 hours in a magnetic field of 5,000 to 50,000 Gauss.

In one exemplary embodiment, the calcined shellfish shell powder may be prepared by calcinating shellfish shells at 800 to 900° C.; cooling the calcined shellfish shells to room temperature; and grinding the shellfish shells to have a size of 100 to 200 mesh.

In one exemplary embodiment, the green tea leaf extract, the *Lespedeza bicolor* leaf extract and the *Chamaecyparis obtusa* leaf extract may be prepared by irradiating green tea leaves, *Lespedeza bicolor* leaves and *Chamaecyparis obtusa* leaves with UV rays for 10 to 30 minutes, respectively; and adding 100 parts by weight of each of the green tea leaves, the *Lespedeza bicolor* leaves and the *Chamaecyparis obtusa* leaves, which are irradiated with UV rays, to 1000 to 2000 parts by weight of water, respectively, and heating the resulting mixtures at 80 to 100° C.

In one exemplary embodiment, 1 to 50 parts by weight of the germanium oxide and 1 to 50 parts by weight of the nano silver may be contained with respect to 100 parts by weight of the green tea leaf extract.

Another aspect of the present invention provides a sterilizing deodorant prepared by the method for preparing a sterilizing deodorant. In one exemplary embodiment, the sterilizing deodorant contains a green tea leaf extract, a *Lespedeza bicolor* leaf extract, a *Chamaecyparis obtusa* leaf extract, a calcined shellfish shell powder, germanium oxide and nano silver, and the germanium oxide and the nano silver are contained at a weight ratio of 1:0.5 to 1:3.

BRIEF DESCRIPTION

Some of the embodiments will be described in detail, with reference to the following figures, wherein like designations denote like members, wherein:

The FIGURE illustrates a method for preparing a sterilizing deodorant according to an exemplary embodiment of the present invention.

DETAILED DESCRIPTION

Hereinafter, embodiments of the present invention will be described in detail. Here, to explain embodiments of the present invention, if it is determined that a detailed description of the related art may unnecessarily obscure the gist of embodiments of the present invention, the detailed description will be omitted.

In addition, terms that will be described below are defined in consideration of functions in embodiments of the present invention, and thus may vary according to a user, an operator's intentions or practices, and therefore the definition of the terms should be made based on the contents throughout the specification that describes embodiments of the present invention.

The term "sterilization" used herein refers to inhibition of growth or proliferation of a substance to be treated, or killing of microorganisms. The term "substance to be treated" used herein is defined to include all of bacteria, fungi, yeast and algae, which can be sterilized and deodorized with a component of the sterilizing deodorant of embodiments of the present invention.

Method for Preparing Sterilization Deodorant

One aspect of the present invention provides a method for preparing a sterilizing deodorant. The FIGURE illustrates a method for preparing a sterilizing deodorant according to an exemplary embodiment of the present invention. Referring to the FIGURE, the method for preparing a sterilizing deodorant includes (S10) preparation of a first mixed solution; (S20) preparation of a second mixed solution; and (S30) filtration. More specifically, the method for preparing a sterilizing deodorant includes (S10) preparing a first mixed solution containing a green tea leaf extract, a *Lespedeza bicolor* leaf extract, a *Chamaecyparis obtusa* leaf extract and a calcined shellfish shell powder; (S20) preparing a second mixed solution by adding germanium oxide and nano silver to the first mixed solution; and (S30) filtering the second mixed solution through a tourmaline filter.

Hereinafter, the method for preparing a sterilizing deodorant according to embodiments of the present invention will be described step by step in detail.

(S10) Preparation of First Mixed Solution

This step is for preparing a first mixed solution containing a green tea leaf extract, a *Lespedeza bicolor* leaf extract, a *Chamaecyparis obtusa* leaf extract and a calcined shellfish shell powder.

In one exemplary embodiment, the first mixed solution may be prepared by preparing a first mixture by mixing 100 parts by weight of a green tea leaf extract, 10 to 50 parts by weight of a *Lespedeza bicolor* leaf extract, 10 to 50 parts by weight of a *Chamaecyparis obtusa* leaf extract and 10 to 70 parts by weight of a calcined shellfish shell powder; and treating the first mixture with any one of electrical energy and magnetic energy.

Hereinafter, ingredients contained in the first mixed solution will be described in detail.

First Mixture

Green Tea Leaf Extract

The green tea leaf extract may be prepared using *Camellia sinensis*. In one exemplary embodiment, the green tea leaf extract may be prepared by irradiating green tea leaves (*Camellia sinensis* leaf) with UV rays having a wavelength of 10 to 398 nm for 10 to 30 minutes; and adding 100 parts by weight of the UV-irradiated green tea leaves to 1000 to 2000 parts by weight of water and heating the resulting mixture at 80 to 100° C. In one exemplary embodiment, the green tea leaf extract may be prepared by heating the mixture to have 10 to 50 vol % with respect to the volume of water before heating. For example, the green tea leaf extract may be prepared by heating until the volume reaches 25 to 30 vol %.

In another exemplary embodiment of the present invention, the first mixture may further include 1 to 20 parts by weight of a green tea leaf powder with respect to 100 parts by weight of the green tea leaf extract. When the powder is contained in the above range, embodiments of the present invention may exhibit more excellent sterilizing and deodorizing effects. In one exemplary embodiment, the green tea leaf powder may be prepared by irradiating green tea leaves with UV rays having a wavelength of 10 to 398 nm for 10 to 30 minutes, and grinding the green tea leaves to have a size of 100 to 200 mesh. Here, the size is defined to represent the largest length.

*Lespedeza bicolor* Leaf Extract

The *Lespedeza bicolor* leaf extract may be prepared using a leaf part of *Lespedeza bicolor*. In one exemplary embodiment, the *Lespedeza bicolor* leaf extract may be prepared by irradiating the *Lespedeza bicolor* leaves with UV rays having a wavelength of 10 to 398 nm for 10 to 30 minutes; and adding 100 parts by weight of the UV-irradiated *Lespedeza bicolor* leaves to 1000 to 2000 parts by weight of water and heating the resulting mixture at 80 to 100° C. In one exemplary embodiment, the *Lespedeza bicolor* leaf extract may be prepared by heating the leaves until the volume reaches 10 to 50 vol % with respect to the volume of water before heating. For example, the *Lespedeza bicolor* leaf extract may be prepared by heating until the volume reaches 25 to 30 vol %.

In one exemplary embodiment, the *Lespedeza bicolor* leaf extract may be contained at 10 to 50 parts by weight with respect to 100 parts by weight of the green tea leaf extract. When the extract is contained in the above range, the sterilizing deodorant of the present invention may exhibit more excellent sterilizing and deodorizing effects.

In still another exemplary embodiment of the present invention, the first mixture may further contain 1 to 20 parts by weight of a *Lespedeza bicolor* leaf powder with respect to 100 parts by weight of the green tea leaf extract. When the powder is contained in the above range, the sterilizing deodorant of embodiments of the present invention may exhibit excellent sterilizing and deodorizing effects. In one exemplary embodiment, the *Lespedeza bicolor* leaf powder may be prepared by irradiating *Lespedeza bicolor* leaves with UV rays having a wavelength of 10 to 398 nm for 10 to 30 minutes, and grinding the leaves to have a size of 100 to 200 mesh.

*Chamaecyparis obtusa* Leaf Extract

The *Chamaecyparis obtusa* leaf extract may be prepared using a leaf part of *Chamaecyparis obtusa*. In one exemplary embodiment, the *Chamaecyparis obtusa* leaf extract may be prepared by irradiating the *Chamaecyparis obtusa* leaves with UV rays having a wavelength of 10 to 398 nm for 10 to 30 minutes; and adding 100 parts by weight of the UV-irradiated *Chamaecyparis obtusa* leaves to 1000 to 2000 parts by weight of water and heating the resulting mixture at 80 to 100° C. In one exemplary embodiment, the *Chamaecyparis obtusa* leaf extract may be prepared by heating the leaves until the volume reaches 10 to 50 vol % with respect to the volume of water before heating. For example, the *Chamaecyparis obtusa* leaf extract may be prepared by heating until the volume reaches 25 to 30 vol %.

In one exemplary embodiment, the *Chamaecyparis obtusa* leaf extract may be contained at 10 to 50 parts by weight with respect to 100 parts by weight of the green tea leaf extract. When the extract is contained in the above range, the sterilizing deodorant of embodiments of the present invention may exhibit excellent sterilizing and deodorizing effects.

In yet another exemplary embodiment, the first mixture may further contain 1 to 20 parts by weight of a *Chamaecyparis obtusa* leaf powder with respect to 100 parts by weight of the green tea leaf extract. When the powder is contained in the above range, the sterilizing deodorant of embodiments of the present invention may exhibit excellent sterilizing and deodorizing effects. In one exemplary embodiment, the *Chamaecyparis obtusa* leaf powder may be prepared by irradiating the *Chamaecyparis obtusa* leaves with UV rays having a wavelength of 10 to 398 nm for 10 to 30 minutes, and grinding the leaves to have a size of 100 to 200 mesh.

Calcined Shellfish Shell Powder

The calcined shellfish shell powder may be prepared by calcinating a shellfish shell for 30 minutes to 1 hour at 800 to 900° C.; cooling the calcined shellfish shell to room temperature (20 to 30° C.); and grinding the shellfish shell to have a size of 100 to 200 mesh.

In embodiments of the present invention, the shellfish may include one or more of bivalves, gastropods and scaphopods. In one exemplary embodiment of the present invention, the shellfish may be one or more of cockles, razor clams, short-necked clams, manila clams, oysters and conches.

In preparation of the shellfish shell powder, cooling after calcination may be performed by any one or more methods selected from cooling after maintenance at room temperature, cooling with cold air, and cooling in cold water.

In one exemplary embodiment, the calcined shellfish shell powder may be contained at 10 to 70 parts by weight with respect to 100 parts by weight of the green tea leaf extract. When the powder is contained in the above range, the sterilizing deodorant of embodiments of the present invention may exhibit excellent sterilizing and deodorizing effects.

In one exemplary embodiment, the treatment with electrical energy is treating the first mixture for 1 to 6 hours in an electric field of 100 to 1000 kV, and the treatment with magnetic energy may be to treat the first mixture for 12 to 24 hours in a magnetic field of 5,000 to 50,000 Gauss. In the treatment with electrical or magnetic energy under the above conditions, water contained in the first mixture may be separated in a nanometer size to increase an absorption effect with respect to a target material generating a foul smell of the sterilizing deodorant of embodiments of the present invention, and to improve permeability to a foul smelling part, ending up with killing a microorganism in the foul smelling part and removing the foul smell. Here, the foul smelling part refers to any one or more selected from a foul smelling material, a foul smelling region, a foul smelling site and/or a foul smelling substance to be treated.

In one exemplary embodiment, the first mixture may be prepared by mixing 100 parts by weight of the green tea leaf extract, 10 to 50 parts by weight of the *Lespedeza bicolor* leaf extract, 10 to 50 parts by weight of the *Chamaecyparis obtusa* leaf extract and 10 to 70 parts by weight of the calcined shellfish shell powder at a rotation speed of 100 to 500 rpm for 1 to 12 hours. Under these conditions, excellent miscibility may be obtained.

(S20) Preparation of Second Mixed Solution

This step is for preparing a second mixed solution by adding germanium oxide and nano silver to the first mixed solution.

Germanium Oxide

The germanium oxide ($GeO_2$) radiates far-infrared rays, and is used to improve sterilizing and deodorizing effects. In one exemplary embodiment, the germanium oxide having an average size of 0.01 to 5 mm may be used.

In one exemplary embodiment, the germanium oxide may be contained at 1 to 50 parts by weight with respect to 100 parts by weight of the green tea leaf extract. When the germanium oxide is contained in the above range, the sterilizing deodorant of embodiments of the present invention may exhibit excellent far-infrared radiation, sterilizing and deodorizing effects.

Nano Silver

Nano silver is included to improve sterilizing and deodorizing effects of embodiments of the present invention. In embodiments of the present invention, the nano silver may be silver particles with a size of 0.1 to 500 nm. The cations (Ag+) of the nano silver are strongly bound to a —SH group, —COOH group, and —OH group of a target substance to be treated, and therefore a cell membrane of the target substance to be treated may be destroyed, and an excellent effect of disturbing the functions of cells may be achieved.

In one exemplary embodiment, the nano silver may be contained at 1 to 50 parts by weight with respect to 100 parts by weight of the green tea leaf extract. When the nano silver is contained in the above range, the sterilizing deodorant of embodiments of the present invention may have excellent sterilizing and deodorizing effects.

In one exemplary embodiment, the germanium oxide and the nano silver may be contained at a weight ratio of 1:0.5 to 1:3. When they are contained in the above ranges, the sterilizing deodorant of embodiments of the present invention has excellent miscibility, an unexpected synergistic effect occurs between ingredients of the sterilizing deodorant, and the sterilizing and deodorizing effects may be significantly increased. When the nano silver is contained at a weight ratio of less than 1:0.5 with respect to the germanium oxide, the synergistic effect of sterilization and deodorization is decreased, and the dispersibility and miscibility of the sterilizing deodorant are decreased. When the nano silver is contained at a weight ratio of more than 1:3 with respect to the germanium oxide, sterilizing and deodorizing effects are not increased any more than the increment in the use of the nano silver, and dispersibility and miscibility of the sterilizing deodorant may be decreased. For example, the nano silver may be contained at a weight ratio of 1:0.5 to 1:1.5.

(S30) Filtration

This step is for filtering the second mixed solution through a tourmaline filter. A conventional tourmaline filter may be used. For example, the second mixed solution may be filtered through a tourmaline powder-filled filter. The tourmaline is a mineral belonging to the hexagonal crystal system, and its chemical component is a complicated boron silicate compounded with iron, magnesium, an alkali metal or aluminum. Such tourmaline is usually formed in a hexagonal or nonagonal shape, and sometimes in triangular pillar or column shape, generates electricity due to friction, and is charged with cations and anions when heated. A purification apparatus using such tourmaline serves to purify and clean water by generating electric current from tourmaline with an electric property when polluted water passes through tourmaline serving as a filter, and instantaneously electrolyzing water to allow alkali ionization.

The sterilizing deodorant may exhibit an excellent anion-generating effect by filtration using the tourmaline filter.

Sterilizing Deodorant Prepared by Method for Preparing Sterilizing Deodorant

Another aspect of the present invention relates to a sterilizing deodorant prepared by the method for preparing a sterilizing deodorant. In one exemplary embodiment, the sterilizing deodorant contains a green tea leaf extract, a *Lespedeza bicolor* leaf extract, a *Chamaecyparis obtusa* leaf extract, a calcined shellfish shell powder, germanium oxide and nano silver.

The sterilizing deodorant of embodiments of the present invention may be prepared as a liquid. The following may provide a method for preparing a liquid sterilizing deodorant capable of reducing and/or removing a foul smell, which is one of the pollutants that are not good for humans, and since the liquid sterilizing deodorant of embodiments of the present invention is formed as a liquid, a foul smell may be effectively removed by applying a suitable content of the sterilizing deodorant according to a degree of foul smell generation.

In one exemplary embodiment, the sterilizing deodorant may contain 100 parts by weight of the green tea leaf extract, 10 to 50 parts by weight of the *Lespedeza bicolor* leaf extract, 10 to 50 parts by weight of the *Chamaecyparis obtusa* leaf extract, 10 to 70 parts by weight of the calcined shellfish shell powder, 1 to 50 parts by weight of the germanium oxide and 1 to 50 parts by weight of the nano silver. The green tea leaf extract, the *Lespedeza bicolor* leaf extract, the *Chamaecyparis obtusa* leaf extract, the calcined shellfish shell powder, the germanium oxide and the nano silver are the same as described above, and thus detail descriptions will be omitted.

In another exemplary embodiment of the present invention, 1 to 10 parts by weight of each of the green tea leaf powder, the *Lespedeza bicolor* leaf powder and the *Chamaecyparis obtusa* leaf powder may be contained with respect to 100 parts by weight of the green tea leaf extract.

In one exemplary embodiment, the germanium oxide and the nano silver are included at a weight ratio of 1:0.5 to 1:3. When the germanium oxide and the nano silver are contained in the above weight ratios, an unexpected synergistic effect may occur between ingredients of the sterilizing deodorant of embodiments of the present invention, and the sterilizing and deodorizing effects may be considerably increased. When the nano silver is contained at a weight ratio of less than 1:0.5 with respect to the germanium oxide, a synergistic effect of sterilization and deodorization is decreased, and dispersibility and miscibility of the sterilizing deodorant are decreased. When the nano silver is contained at a weight ratio of more than 1:3 with respect to the germanium oxide, the sterilizing and deodorizing effects are not increased any more than the increment in the use of the nano silver, and the dispersibility and miscibility of the sterilizing deodorant may be decreased. For example, the nano silver may be contained at a weight ratio of 1:0.5 to 1:1.5.

The sterilizing deodorant prepared by the method for preparing a sterilizing deodorant according to embodiments of the present invention may have excellent productivity and economic feasibility, be good for health due to an excellent far-infrared and anionic radiation effect, have excellent environmental friendliness, be harmless to humans, have excellent sterilizing and foul smell-removal efficiency, enable removal and sterilization of a foul smell with respect to various substances, and have excellent sustainability of sterilization and foul smell removal.

Hereinafter, configurations and actions of embodiments of the present invention will be described in further detail with reference to exemplary examples of the present invention. However, these examples are merely provided as preferable examples, and it is to be understood that embodiments of the present invention is not limited to the following examples by any means.

EXAMPLES AND COMPARATIVE EXAMPLES

Example 1

Green tea leaf extract: Leaves of *Camellia sinensis* were washed to remove impurities, and irradiated with UV rays having a wavelength of 190 to 210 nm for 15 minutes using a lamp. A green tea leaf extract was prepared by adding 100 parts by weight of the UV-irradiated leaves of *Camellia sinensis* to 1000 parts by weight of distilled water, heating the resulting solution to 100° C., heating the resulting solution to 25 vol % with respect to the volume of distilled water before heating, and filtering the resulting solution using a filter.

*Lespedeza bicolor* leaf extract: Leaves of *Lespedeza bicolor* were washed to remove impurities, and irradiated with UV rays having a wavelength of 190 to 210 nm for 15 minutes using a lamp. A *Lespedeza bicolor* leaf extract was prepared by adding 100 parts by weight of the UV-irradiated leaves of *Lespedeza bicolor* to 1000 parts by weight of distilled water, heating the resulting solution to 100° C., heating the resulting solution to 25 vol % with respect to the volume of distilled water before heating, and filtering the resulting solution using a filter. *Chamaecyparis obtusa* leaf extract: Leaves of *Chamaecyparis obtusa* were washed to remove impurities, and irradiated with UV rays having a wavelength of 190 to 210 nm for 15 minutes using a lamp. A *Chamaecyparis obtusa* leaf extract was prepared by adding 100 parts by weight of the UV-irradiated leaves of *Chamaecyparis obtusa* to 1000 parts by weight of distilled water, heating the resulting solution to 100° C., heating the resulting solution to 25 vol % with respect to the volume of distilled water before heating, and filtering the resulting solution using a filter.

Calcined shellfish shell powder: A calcined shellfish shell powder was prepared by washing shells of *Crassostrea gigas* to remove impurities, calcining the washed shells at 850° C. for 45 minutes, maintaining the resulting product at room temperature to cool to a temperature of 25° C., and grinding the resulting product to an average size of 150 mesh.

Manufacture of Sterilizing Deodorant

A first mixture was prepared by mixing 100 parts by weight of the green tea leaf extract, 25 parts by weight of the *Lespedeza bicolor* leaf extract, 25 parts by weight of the *Chamaecyparis obtusa* leaf extract and 45 parts by weight of the calcined shellfish shell powder at a rotation speed of 290 to 310 rpm for 6 hours. A first mixed solution was prepared by treating the first mixture with electrical energy in an electric field of 500 kV for 3 hours.

Afterward, a second mixed solution was prepared by adding 15 parts by weight of germanium oxide and 15 parts by weight of nano silver (1:1 weight ratio) with respect to 100 parts by weight of the green tea leaf extract and mixing them. Then, a liquid sterilizing deodorant was prepared by filtering the second mixed solution using a tourmaline filter.

Example 2

A liquid sterilizing deodorant was prepared by the same method as described in Example 1, except that a first mixed solution was prepared by treating the first mixture with magnetic energy in a magnetic field of 30,000 Gauss for 12 hours.

Example 3

A liquid sterilizing deodorant was prepared by the same method as described in Example 1, except that a first mixed solution was prepared by treating the first mixture with electrical energy and then with magnetic energy in a magnetic field of 30,000 Gauss for 12 hours.

Example 4

A liquid sterilizing deodorant was prepared by the same method as described in Example 1, except that a first mixed solution was prepared by treating the first mixture with magnetic energy in a magnetic field of 30,000 Gauss for 12 hours and then with electrical energy in an electric field of 500 kV for 3 hours.

Examples 5 to 7

Green tea leaf powder: Leaves of *Camellia sinensis* were washed to remove impurities, and irradiated with UV rays having a wavelength of 190 to 210 nm for 15 minutes using a lamp. The UV-irradiated leaves of *Camellia sinensis* were ground to have a size of 150 mesh, thereby preparing a green tea leaf powder.

*Lespedeza bicolor* leaf powder: Leaves of *Lespedeza bicolor* were washed to remove impurities, and irradiated with UV rays having a wavelength of 190 to 210 nm for 15 minutes using a lamp. The UV-irradiated leaves of *Lespedeza bicolor* were ground to have a size of 150 mesh, thereby preparing a *Lespedeza bicolor* leaf powder.

*Chamaecyparis obtusa* leaf extract: Leaves of *Chamaecyparis obtusa* were washed to remove impurities, and irradiated with UV rays having a wavelength of 190 to 210 nm for 15 minutes using a lamp. The UV-irradiated leaves of *Chamaecyparis obtusa* were ground to have a size of 150 mesh, thereby preparing a *Chamaecyparis obtusa* leaf powder.

Example 5

A first mixture was prepared by mixing 100 parts by weight of a green tea leaf extract, 45 parts by weight of a calcined shellfish shell powder, 25 parts by weight of a *Lespedeza bicolor* leaf extract, 3 parts by weight of a *Lespedeza bicolor* leaf powder and 25 parts by weight of a *Chamaecyparis obtusa* leaf extract at a rotation speed of 290 to 310 rpm for 6 hours.

A first mixed solution was prepared by treating the first mixture with magnetic energy in a magnetic field of 30,000 Gauss for 12 hours. Afterward, a second mixed solution was prepared by adding 15 parts by weight of the germanium oxide and 15 parts by weight of the nano silver with respect to 100 parts by weight of the green tea leaf extract to be mixed with the first mixed solution. Then, a liquid sterilizing deodorant was prepared by filtering the second mixed solution using a tourmaline filter.

Example 6

A sterilizing deodorant was prepared by the same method as described in Example 5, except that a first mixture was prepared by mixing 100 parts by weight of a green tea leaf extract, 45 parts by weight of a calcined shellfish shell powder, 25 parts by weight of a *Lespedeza bicolor* leaf extract, 25 parts by weight of a *Chamaecyparis obtusa* leaf extract and 3 parts by weight of a *Chamaecyparis obtusa* leaf powder at a rotation speed of 290 to 310 rpm for 6 hours.

Example 7

A sterilizing deodorant was prepared by the same method as described in Example 5, except that a first mixture was prepared by adding 100 parts by weight of a green tea leaf extract, 45 parts by weight of a calcined shellfish shell powder, 25 parts by weight of a *Lespedeza bicolor* leaf extract, 3 parts by weight of a *Lespedeza bicolor* leaf powder, 25 parts by weight of a *Chamaecyparis obtusa* leaf extract and 3 parts by weight of a *Chamaecyparis obtusa* leaf powder and mixing them at a rotation speed of 290 to 310 rpm for 6 hours.

Comparative Example 1

A liquid sterilizing deodorant was prepared by the same method as described in Example 1, except that germanium oxide was not applied.

Comparative Example 2

A liquid sterilizing deodorant was prepared by the same method as described in Example 1, except that nano silver was not applied.

Comparative Example 3

A liquid sterilizing deodorant was prepared by the same method as described in Example 1, except that germanium oxide and nano silver were not applied.

Comparative Example 4

A liquid sterilizing deodorant was prepared by the same method as described in Example 1, except that 15 parts by weight of germanium oxide and 5 parts by weight of nano silver (1:0.3 weight ratio) were applied with respect to 100 parts by weight of the green tea leaf extract.

Comparative Example 5

A liquid sterilizing deodorant was prepared by the same method as described in Example 1, except that 10 parts by weight of germanium oxide and 35 parts by weight of nano silver (1:3.5 weight ratio) were applied with respect to 100 parts by weight of the green tea leaf extract.

Experimental Example (1): Deodorizing Performance Test

For sterilizing deodorants prepared in Examples 1 to 7 and Comparative Examples 1 to 5, deodorizing performance with respect to basic odorous substances such as ammonia, and trimethylamine and acidic odorous substances such as hydrogen sulfide and methyl mercaptan was measured by the following method.

As a test apparatus, Model 801 (GASTEC Co., Japan) was used, ammonia, which is a foul smelling source, was injected into the apparatus for a deodorization test (40 cm×40 cm×60 cm), and controlled to have a concentration of 50 ppm using a GASTEC apparatus. Trimethylamine, hydrogen sulfide and methyl mercaptan were injected into respective deodorizing containers in the same manner and controlled to have a concentration of 100 ppm. 30 ml each of the liquid sterilizing deodorants prepared in Examples 1 to 7 and Comparative Examples 1 to 5 were sprayed in the apparatus suitably controlled to have the initial concentration using a sprayer, and then concentrations were measured after 30 minutes, 1 hour, 3 hours and 6 hours. The results are shown in Tables 1 and 2. Meanwhile, the laboratory conditions were maintained at an indoor temperature of 22±5° C. and a relative humidity of 43±5%.

TABLE 1

| Type | | Ammonia (ppm) | Trimethylamine (ppm) | Hydrogen sulfide (ppm) | Methyl mercaptan (ppm) |
|---|---|---|---|---|---|
| Example 1 | Initial | 100 | 100 | 100 | 100 |
|  | 30 min | 88 | 89 | 86 | 87 |
|  | 1 hr | 74 | 76 | 75 | 77 |
|  | 3 hrs | 63 | 65 | 69 | 60 |
|  | 6 hrs | 46 | 41 | 43 | 45 |
| Example 2 | Initial | 100 | 100 | 100 | 100 |
|  | 30 min | 86 | 85 | 85 | 87 |
|  | 1 hr | 72 | 75 | 73 | 76 |
|  | 3 hrs | 63 | 65 | 63 | 60 |
|  | 6 hrs | 46 | 45 | 41 | 42 |
| Example 3 | Initial | 100 | 100 | 100 | 100 |
|  | 30 min | 86 | 86 | 87 | 87 |
|  | 1 hr | 72 | 73 | 73 | 72 |
|  | 3 hrs | 55 | 56 | 63 | 56 |
|  | 6 hrs | 38 | 39 | 39 | 41 |
| Example 4 | Initial | 100 | 100 | 100 | 100 |
|  | 30 min | 89 | 87 | 89 | 88 |
|  | 1 hr | 76 | 71 | 71 | 72 |
|  | 3 hrs | 63 | 61 | 62 | 60 |
|  | 6 hrs | 37 | 39 | 39 | 43 |
| Example 5 | Initial | 100 | 100 | 100 | 100 |
|  | 30 min | 91 | 89 | 86 | 91 |
|  | 1 hr | 79 | 77 | 77 | 68 |
|  | 3 hrs | 52 | 54 | 61 | 59 |
|  | 6 hrs | 37 | 35 | 41 | 39 |
| Example 6 | Initial | 100 | 100 | 100 | 100 |
|  | 30 min | 88 | 89 | 86 | 87 |
|  | 1 hr | 72 | 73 | 74 | 75 |
|  | 3 hrs | 61 | 57 | 59 | 58 |
|  | 6 hrs | 37 | 36 | 41 | 38 |

TABLE 2

| Type | | Ammonia (ppm) | Trimethyl-amine (ppm) | Hydrogen sulfide (ppm) | Methyl mercaptan (ppm) |
|---|---|---|---|---|---|
| Example 7 | Initial | 100 | 100 | 100 | 100 |
|  | 30 min | 86 | 83 | 85 | 85 |
|  | 1 hr | 69 | 71 | 73 | 73 |
|  | 3 hrs | 56 | 63 | 63 | 57 |
|  | 6 hrs | 36 | 35 | 39 | 33 |
| Comparative Example 1 | Initial | 100 | 100 | 100 | 100 |
|  | 30 min | 91 | 89 | 91 | 91 |
|  | 1 hr | 81 | 82 | 82 | 81 |
|  | 3 hrs | 69 | 71 | 70 | 69 |
|  | 6 hrs | 52 | 55 | 52 | 53 |
| Comparative Example 2 | Initial | 100 | 100 | 100 | 100 |
|  | 30 min | 91 | 92 | 90 | 91 |
|  | 1 hr | 80 | 81 | 81 | 79 |
|  | 3 hrs | 68 | 67 | 67 | 65 |
|  | 6 hrs | 53 | 52 | 51 | 54 |
| Comparative Example 3 | Initial | 100 | 100 | 100 | 100 |
|  | 30 min | 90 | 91 | 90 | 91 |
|  | 1 hr | 81 | 80 | 79 | 80 |
|  | 3 hrs | 69 | 69 | 67 | 67 |
|  | 6 hrs | 56 | 55 | 53 | 53 |

TABLE 2-continued

| Type | | Ammonia (ppm) | Trimethyl-amine (ppm) | Hydrogen sulfide (ppm) | Methyl mercaptan (ppm) |
|---|---|---|---|---|---|
| Comparative Example 4 | Initial | 100 | 100 | 100 | 100 |
| | 30 min | 90 | 92 | 90 | 91 |
| | 1 hr | 81 | 80 | 79 | 80 |
| | 3 hrs | 69 | 72 | 66 | 67 |
| | 6 hrs | 55 | 53 | 53 | 54 |
| Comparative Example 5 | Initial | 100 | 100 | 100 | 100 |
| | 30 min | 92 | 89 | 91 | 92 |
| | 1 hr | 81 | 79 | 81 | 83 |
| | 3 hrs | 67 | 70 | 68 | 68 |
| | 6 hrs | 56 | 54 | 55 | 55 |

Referring to the results shown in Tables 1 and 2, it can be seen that deodorization performance of the liquid sterilizing deodorants prepared in Example 1 to 7 of embodiments of the present invention with respect to ammonia, trimethylamine, hydrogen sulfide and methyl mercaptan is better than those of Comparative Examples 1 to 5. On the other hand, it was found that Comparative Examples 1 to 5 in which one or more among germanium oxide and nano silver of embodiments of the present invention were not applied, compared to Examples 1 to 7, deodorization performance with respect to ammonia, trimethylamine, hydrogen sulfide and methyl mercaptan was reduced. In addition, it can be seen that Comparative Examples 4 and 5 in which the weight ratio of the germanium oxide and the nano silver were applied beyond the above range of the weight ratio, compared to Examples 1 to 7, deodorization performance with respect to ammonia, trimethylamine, hydrogen sulfide and methyl mercaptan was reduced.

Experimental Example (2): Acute Toxicity Test

An acute toxicity test was performed on animals using the liquid sterilizing deodorants prepared by Examples 1 to 7, and their toxicities were detected.

For test animals used in the acute toxicity test, sixty 5-week-old male (body weight: 105±4 g) and female (body weight: 95±3 g) SPF SD-type rats (purchased from Somang Livestock) were used, the liquid sterilizing deodorants of embodiments of the present invention prepared in Examples 1 to 4 were tested using distilled water as a negative control.

First, the rats were acclimated for approximately 1 week in animal cages under conditions of a temperature of 22±2° C., a relative humidity of 53±2% and a light/night cycle by fluorescent lighting (09:00 on-18:00 off), and an illuminance of 150 to 300 lux. Only healthy ones among the rats were selected and divided into groups to have the same average body weight, and after forced oral administration for 14 days at a dose of 20 ml/kg once a day, a change in general conditions, toxicity symptoms, mobility, appearance, autonomic nerves, a change in body weight and the presence of dead animals were examined.

According to the test results, during the test, an approximately 7% change in body weight was shown but did not have significance, there were no dead animals among the experimental animals fed the sterilizing deodorant, and no specific general symptoms were not shown, thus it was determined that the liquid sterilizing deodorants prepared in Examples 1 to 7 have no toxicity.

Experimental Example (3): Eye Irritation Test

An eye irritation test was performed with respect to the sterilizing deodorants prepared in Examples 1 to 7 of embodiments of the present invention to check a degree of irritation in animals.

Experimental animals used in the eye irritation test were white rabbits. First, experimental animals were obtained and acclimated in animal cages for two weeks, followed by observing general conditions during the acclimation. Through the observation, healthy animals were only used for the test. Conditions of lesions of the corneas, conjunctivas and irises of the left and right eyes of the rabbits were examined 24 hours before the test, and thereby eight white rabbits which had healthy right and left eyes and a body weight of 2.5±0.1 kg were selected as the experimental animals.

0.1 ml each of the liquid sterilizing deodorants prepared in Examples 1 to 7 were administered dropwise into eyes of each group of two rabbits, and after 30 seconds, the right and left eyes of four rabbits were washed with 20 ml of normal saline for 1 minute, and the other four rabbits were not washed. The other eyes to which test substances were not administered were used as a control, and after administration of the test substances, conditions of the eyes were observed on day 1, 2, 3, 4, 5, 6 and 7. Afterward, general symptoms, feed and water intake were observed every third day for more than 13 days.

Rating for eye lesions and criteria for the degree of irritation were evaluated according to "Guidelines for Toxicity Studies of Drugs" provided by Korea Food and Drug Administration (KFDA) guidelines (No. 1999-61), and the standard work instructions (I) published by the KFDA, and the degree of irritation was determined using the irritation index on ocular lesions and ocular irritation rating. That is, the scores of irritation for the cornea (max. 80), the iris (max. 10), and the conjunctiva (max. 20) of each animal at each observation time were obtained using the ocular irritation rating, thereby the total score thereof was calculated for each animal. The value of the total score/the number of tested animals is referred to as mean ocular irritation index (M.O.I.). During observation, the degree of ocular irritation was evaluated using the acute ocular irritation index (A.O.I.), which is the maximum value of the M.O.I.

According to the test results, after treatment of the liquid sterilizing deodorants prepared in Examples 1 to 7 on the rabbit eyes, no phenomenon caused by irritation was not shown, no dead animals were observed, and no abnormal symptoms in the cornea, iris, and conjunctiva of each animal on day 1, 2, 3, 4, 5, 6, and 7 after ocular treatment were observed. The A.O.I. value was "0," indicating that the liquid sterilizing deodorants prepared in Examples 1 to 7 of embodiments of the present invention was determined as a non-irritant.

Experimental Example (4): Dermal Irritation Test

A skin irritation test was carried out to examine the degree of irritation of the liquid sterilizing deodorants prepared in Examples 1 to 7 of embodiments of the present invention in animals.

Four white rabbits with a body weight of 2.5±0.1 kg were used as experimental animals for a skin irritation test. First, experimental animals were obtained, and acclimated for 1 week in animal cages. During acclimatization, general conditions were observed, and only healthy animals were used for the test. The rabbits were shaved 24 hours before the treatment with a test material, and their skin was divided into treated sections and control sections. Then, 0.5 ml each of the liquid sterilizing deodorants prepared in Examples 1 to 7 was applied once to an administration site in the treated section, the same amount of sterilized saline was applied to the non-treated control section. The sterilizing deodorant and normal saline were applied, covered with a solid thin film and fixed with a tape, followed by application for a certain time. After the application, the coated part was mildly washed with saline. After the treatment with the test material, the appearance, feed and water intake and clinical symptoms were observed every day for one week, abnormalities in the treated sections and the control sections were checked by visual observation on day 7 after application.

Evaluation of skin reactions was determined at 24 hours and 72 hours according to the "Guidelines for Toxicity Studies of Drugs." In addition, determination of the degree of dermal irritation was carried out according to the method of calculating the Draize's primary irritation index (P.I.I.), which is commonly used.

According to the test results, irritation such as redness, scab formation and edemas on the test material-applied sites were not identified, and a dermal primary irritation score was evaluated as "0" according to the Draize's P.I.I. From the test results, the liquid sterilizing deodorants prepared in Examples 1 to 7 of embodiments of the present invention were determined not to have toxicity or cause irritation with respect to the experimental animals, and it can be seen that they did not have any side effect on an environment or an animal.

Experimental Example (5): Antifungal Test

An antifungal test was carried out for the sterilizing deodorants of Examples 1 to 7 of embodiments of the present invention by the method which will be described below.

Each sample of the liquid sterilizing deodorants prepared in Examples 1 to 7 was applied to a filter, placed on a fungal growth medium in a size of 4×4 cm. The samples were inoculated with 5 types of fungal spore suspensions, grown in an incubator at 29±1° C. with a relative humidity of 85% for 4 weeks, followed by chronological observation of fungal growth on a surface of the samples every week for four weeks. The results are shown in Tables 3 to 9. Here, as the sample, a solution prepared by dissolving 1 part by weight of each of the sterilizing deodorants of Examples 1 to 7 with respect to 100 parts by weight of distilled water was used, and a potato dextrose agar (PDA) medium was used as the fungal growth medium.

Here, the 5 types of the fungal spore suspensions were suspensions of 5 types of strains such as *aspergillus niger* ATCC 9642, *penicillium pinophilum* ATCC 11797, *chaetomium globosum* ATCC 6205, *gliosiadium virens* ATCC 9645, and *aureobasidium pullulans* ATCC 15233.

TABLE 3

Antifungal test (Example 1)
Culture period (week)

| Test item | After 1 week | After 2 weeks | After 3 weeks | After 4 weeks |
|---|---|---|---|---|
| Test result | 0 | 0 | 0 | 0 |
| Test method | ASTM G-21 | | | |

TABLE 4

Antifungal test (Example 2)
Culture period (week)

| Test item | After 1 week | After 2 weeks | After 3 weeks | After 4 weeks |
|---|---|---|---|---|
| Test result | 0 | 0 | 0 | 0 |
| Test method | ASTM G-21 | | | |

TABLE 5

Antifungal test (Example 3)
Culture period (week)

| Test item | After 1 week | After 2 weeks | After 3 weeks | After 4 weeks |
|---|---|---|---|---|
| Test result | 0 | 0 | 0 | 0 |
| Test method | ASTM G-21 | | | |

TABLE 6

Antifungal test (Example 4)
Culture period (week)

| Test item | After 1 week | After 2 weeks | After 3 weeks | After 4 weeks |
|---|---|---|---|---|
| Test result | 0 | 0 | 0 | 0 |
| Test method | ASTM G-21 | | | |

TABLE 7

Antifungal test (Example 5)
Culture period (week)

| Test item | After 1 week | After 2 weeks | After 3 weeks | After 4 weeks |
|---|---|---|---|---|
| Test result | 0 | 0 | 0 | 0 |
| Test method | ASTM G-21 | | | |

TABLE 8

Antifungal test (Example 6)
Culture period (week)

| Test item | After 1 week | After 2 weeks | After 3 weeks | After 4 weeks |
|---|---|---|---|---|
| Test result | 0 | 0 | 0 | 0 |
| Test method | ASTM G-21 | | | |

TABLE 9

Antifungal test (Example 7)
Culture period (week)

| Test item | After 1 week | After 2 weeks | After 3 weeks | After 4 weeks |
|---|---|---|---|---|
| Test result | 0 | 0 | 0 | 0 |
| Test method | ASTM G-21 | | | |

Referring to the results shown in Tables 3 to 9, it can be seen that no fungal growth was shown in the 5 types of fungal spore suspensions inoculated with each of the sterilizing deodorants prepared in Examples 1 to 7 of embodiments of the present invention, indicating that the sterilizing deodorants prepared in Examples 1 to 7 have excellent antimicrobial (antifungal) characteristics.

The sterilizing deodorant prepared by the method for preparing a sterilizing deodorant according to embodiments of the present invention can be excellent in productivity, economic feasibility, far-infrared and anionic radiation effects, miscibility, and a sterilizing effect and foul smell removal efficiency, perform foul smell removal and sterilization with respect to various substances, and have excellent sustainability of sterilization and foul smell removal.

It will be understood by those skilled in the art that simple changes or modifications may be easily made, and are considered to be included in the scope of embodiments of the present invention.

What is claimed is:

1. A method for preparing a sterilizing deodorant, comprising:
preparing a first mixed solution containing a green tea leaf extract, a *Lespedeza bicolor* leaf extract, a *Chamaecyparis obtusa* leaf extract and a calcined shellfish shell powder;
preparing a second mixed solution by adding germanium oxide and nano silver to the first mixed solution; and
filtering the second mixed solution through a tourmaline filter,
wherein the germanium oxide and the nano silver are contained at a weight ratio of 1:0.5 to 1:3.

2. The method of claim 1, wherein the preparation of the first mixed solution comprises:
preparing a first mixture by mixing 100 parts by weight of a green tea leaf extract, 10 to 50 parts by weight of a *Lespedeza bicolor* leaf extract, 10 to 50 parts by weight of a *Chamaecyparis obtusa* leaf extract and 10 to 70 parts by weight of a calcined shellfish shell powder; and
treating the first mixture with one or more of electrical energy and magnetic energy,
wherein the treatment with electrical energy is treating the first mixture in an electric field of 100 to 1000 kV for 1 to 6 hours, and
the treatment with magnetic energy is treating the first mixture in a magnetic field of 5,000 to 50,000 Gauss for 12 to 24 hours.

3. The method of claim 1, wherein the preparation of the calcined shellfish shell powder comprises:
calcinating shells of shellfish at 800 to 900° C.;
cooling the calcined shells of shellfish to room temperature; and
grinding the shells of shellfish to have a size of 100 to 200 mesh.

4. The method of claim 1, wherein the preparation of the green tea leaf extract, the *Lespedeza bicolor* leaf extract and the *Chamaecyparis obtusa* leaf extract comprises:
irradiating each of green tea leaves, *Lespedeza bicolor* leaves and *Chamaecyparis obtusa* leaves with UV rays for 10 to 30 minutes; and
adding 100 parts by weight of each of the UV-irradiated green tea leaves, *Lespedeza bicolor* leaves and *Chamaecyparis obtusa* leaves to 1000 to 2000 parts by weight of water, respectively, and heating the resulting mixtures at 80 to 100° C.

5. The method of claim 1, wherein 1 to 50 parts by weight of germanium oxide and 1 to 50 parts by weight of nano silver are added with respect to 100 parts by weight of the green tea leaf extract.

6. A sterilizing deodorant, comprising:
a green tea leaf extract, a *Lespedeza bicolor* leaf extract, a *Chamaecyparis obtusa* leaf extract, a calcined shellfish shell powder, germanium oxide and nano silver,
wherein the germanium oxide and the nano silver are contained at a weight ratio of 1:0.5 to 1:3.

* * * * *